(12) United States Patent
Marshall et al.

(10) Patent No.: US 7,666,993 B2
(45) Date of Patent: Feb. 23, 2010

(54) CYNOMOLGUS PROSTATE SPECIFIC ANTIGEN

(75) Inventors: Deborah J. Marshall, Blue Bell, PA (US); Linda A. Snyder, Pottstown, PA (US)

(73) Assignee: Centocor, Inc., Malvern, PA (US)

( * ) Notice: Subject to any disclaimer, the term of this patent is extended or adjusted under 35 U.S.C. 154(b) by 114 days.

(21) Appl. No.: 11/972,107

(22) Filed: Jan. 10, 2008

(65) Prior Publication Data
US 2009/0118468 A1 May 7, 2009

Related U.S. Application Data

(62) Division of application No. 11/138,242, filed on May 26, 2005, now Pat. No. 7,342,107.

(60) Provisional application No. 60/575,079, filed on May 27, 2004.

(51) Int. Cl.
*C07K 14/00* (2006.01)
(52) U.S. Cl. .................................................. 530/350
(58) Field of Classification Search ................. 530/350
See application file for complete search history.

(56) References Cited

U.S. PATENT DOCUMENTS

| | | | |
|---|---|---|---|
| 5,266,489 A | 11/1993 | Rey-Senelonge et al. | |
| 5,558,860 A | 9/1996 | Ross et al. | |
| 5,585,254 A | 12/1996 | Maxwell et al. | |
| 5,616,326 A | 4/1997 | Spibey | |
| 5,693,530 A | 12/1997 | Schat et al. | |
| 5,744,143 A | 4/1998 | Ross et al. | |
| 5,756,103 A | 5/1998 | Paoletti et al. | |
| 5,766,599 A | 6/1998 | Paoletti et al. | |
| 5,795,872 A | 8/1998 | Ricigliano et al. | |
| 5,858,368 A | 1/1999 | Smith et al. | |
| 5,922,321 A * | 7/1999 | Bandman et al. | 424/94.64 |
| 5,958,425 A | 9/1999 | Ross et al. | |
| 5,990,091 A | 11/1999 | Tartaglia et al. | |
| 6,020,172 A | 2/2000 | Both | |
| 6,086,890 A | 7/2000 | Mittal et al. | |
| 6,086,891 A | 7/2000 | Hurwitz et al. | |
| 6,099,847 A | 8/2000 | Tobin et al. | |
| 6,140,114 A | 10/2000 | Klatzmann et al. | |
| 6,221,136 B1 | 4/2001 | Liu et al. | |
| 6,274,147 B1 | 8/2001 | Vakharia et al. | |
| 2002/0099189 A1 | 7/2002 | Savizky et al. | |
| 2003/0064397 A1 | 4/2003 | Spancake et al. | |

FOREIGN PATENT DOCUMENTS

| | | |
|---|---|---|
| WO | WO 87/06262 | 10/1987 |
| WO | WO 93/19183 | 9/1993 |
| WO | WO 95/20660 | 8/1995 |
| WO | WO 97/35021 | 9/1997 |

OTHER PUBLICATIONS

Lundwall, et al., "Molecular cloning of human prostate specific antigen cDNA," FEBS Letters, 214(2): 317-322 (1987).
Xiang, et al., "A Replication-Defective Human Adenovirus Recombinant Serves as a Highly Efficacious Vaccine Carrier," Virology, 219: 220-227 (1996).
Fries, et al., "Human safety and immunogenicity of a canarypox-rabies glycoprotein recombinant vaccine: an alternative poxvirus vector system," Vaccine, 14(5): 428-434 (1996).
Gönczöl, et al., "Preclinical evaluation of an ALVAC (canarypox)-human cytomegalovirus glycoprotein B vaccine candidate," Vaccine 13(12): 1080-1085 (1995).
Xue, et al., "Induction of Human Cytotoxic T Lymphocytes Specific for Prostate-Specific Antigen," The Prostate, 30: 73-78 (1997).
Lubeck, et al., "Immunogenicity and Efficacy Testing in Chimpanzees of an Oral Hepatitis B Vaccine Based on Live Recombinant Adenovirus," Proceedings of the National Academy of Science USA, 86: 6763-6767 (1989).
Cooney, et al., "Enhanced Immunity to Human Immunodeficiency Virus (HIV) Envelope Elicited by a Combined Vaccine Regimen Consisting of Priming with a Vaccinia Recombinant Expressing HIV Envelope and Boosting with gp160 protein," Proceedings of the National Academy of Science USA, 90: 1882-1886 (1993).
Wei, et al., "Tissue-specific expression of the human prostate-specific antigen gene in transgenic mice: Implications for tolerance and immunotherapy," Proceedings of the National Academy of Science USA, 94: 6369-6374 (1997).
Sioud, et al., "Generation of an effective anti-tumor immunity after immunization with xenogeneic antigens," European Journal of Immunology, 33: 38-45 (2003).
Wolchok, et al, "DNA Vaccines: An Active Immunization Strategy for Prostate Cancer," Seminars in Oncology, 30(5): 659-666 (2003).
Watt, et al, "Human Prostate-Specific Antigen: Structural and Functional Similarity with Serine Proteases," Proceedings of the National Academy of Science, 83: 3166-3170 (1986).
Pialoux, et al., "A Prime-Boost Approach to HIV Preventive Vaccine Using a Recombinant Canarypox Virus Expressing Glycoprotein 160 (MN) followed by a Recombinant Glycoprotein 160 (MN/LAI)," Aids Research and Human Retroviruses, 11(3): 373-381 (1995).
David, et al., "Unusual Alternative Splicing within the Human Kallikrein Genes *KLK2* and *KLK3* Gives Rise to Novel Prostate-specific Proteins," The Journal of Biological Chemistry, 277(20): 18084-18090 (2002).
Andersson, et al., "Immunogenicity and Protective Efficacy of a Human Immunodeficiency Virus Type 2 Recombinant Canarypox (ALVAC) Vaccine Candidate in Cynomolgus Monkeys," The Journal of Infectious Diseases, 174: 977-985 (1996).
Judith A. Clements, "The Glandular Kallikrein Family of Enzymes: Tissue-Specific Expression and Hormonal Regulation," Endocrine Reviews, 10(4): 393-419 (1989).
Correale, et al., "In Vitro Generation of Human Cytotoxic T Lymphocytes Specific for Peptides Derived from Prostate-Specific Antigen," Journal of the National Cancer Institute, 89(4): 293-300 (1997).

(Continued)

*Primary Examiner*—Sean E Aeder
(74) *Attorney, Agent, or Firm*—Kirk Baumeister

(57) ABSTRACT

Isolated polynucleotides encoding Cynomolgus monkey prostate specific antigen and polypeptides obtainable from the polynucleotides and uses are disclosed.

4 Claims, 3 Drawing Sheets

OTHER PUBLICATIONS

Gentz, et al., "Bioassay for Trans-Activation Using Purified Human Immunodeficiency Virus tat-Encoded protein: Trans-activation requires mRNA Synthesis," Proceedings of the National Academy of Science USA, 86: 821-824 (1989).

Graham, et al., "Vaccination of Vaccinia-Naïve Adults with Human Immunodeficiency Virus Type I gp160 Recombinant Vaccinia Virus in a Blinded, Controlled, Randomized Clinical Trial," Journal of Infectious Diseases, 166: 244-252 (1992).

Habenicht, et al., "Induction of Estrogen-Related Hyperplastic changes in the Prostate of the Cynomolgus Monkey (*Macaca fascicularis*) by Androstenedione and its Antagonization by Aromatase Inhibitor 1-Methyl-Androsta-1,4-Diene-3, 17-Dione," The Prostate, 11: 313-326 (1987).

Liu, et al., "Immunotherapy of tumors with vaccine based on quail homologous vascular endothelial growth factor receptor-2," Blood, 102(5): 1815-1823 (2003).

McElrath, et al., "Immune Responses Elicited by Recombinant Vaccinia-Human Immunodeficiency Virus (HIV) Envelope and HIV Envelope Protein: Analysis of the Durability of Responses and Effect of Repeated Boosting," Journal of Infectious Diseases, 169: 41-47 (1994).

Prevec, et al., "A Recombinant Human Adenovirus Vaccine against Rabies," Journal of Infectious Diseases, 161: 27-30 (1990).

Stamey, et al., "Prostate-Specific Antigen As a Serum Marker for Adenocarcinoma of the Prostate," The New England Journal of Medicine, 317(15): 909-916 (1987).

Watt, et al., "Human Prostate-Specific Antigen: Structural and Functional Similarity with Serine Proteases," Proceedings of the National Academy of Sciences USA, 83: 3166-3170 (1986).

Wilson, et al., "The Structure of an Antigenic Determinant in a Protein," Cell, 37: 767-778 (1984).

Riegman, et al., "Molecular Cloning and Characterization of Novel Prostate Antigen cDNA's," Biochemical and Biophysical Research Communications, 155(1): 181-188 (1988).

Kaplitt, et al., "Expression of a Functional Foreign Gene In Adult Mammalian Brain following in Vivo Transfer via a Herpes Simplex Virus Type I Defective Viral Vector," Molecular and Cellular Neurosciences, 2: 320-330 (1991).

Wolchok, et al., "Alternative roles for interferon-gamma in the immune response to DNA vaccines encoding related melanosomal antigens," Cancer Immunity, 1 : 9-18 (2001).

Gilardi-Hebenstreit, et al., "Construction of a defective adenovirus vector expressing the pseudorabies virus glycoprotein gp50 and its use as a live vaccine," Journal of General Virology, 71: 2425-2431 (1990).

Kamischke, et al., "The Cynomolgus Monkey Prostate Under Physiological and Hypogonadal Conditions: an Ultrasonographic Study," The Journal of Urology, 157: 2340-2344 (1997).

Kim, et al., "Molecular and immunological analysis of genetic prostate specific antigen (PSA) vaccine," Oncogene, 17: 3125-3135 (1998).

Kim, et al., "Induction of immune responses and safety profiles in rhesus macaques immunized with a DNA vaccine expressing human prostate specific antigen," Oncogene, 20: 4497-4506 (2001).

Centrotide® Package Insert, Manufactured for: Serono, Inc., Rockland, Massachusetts, (Jun. 28, 2004).

"Aeterna prostate treatment accepted by FDA," Pharmaceutical Business Review, www. pharmaceutical-business-review.com/article, Jan. 16, 2007.

Jungwirth, et al., "Inhibition of growth of androgen-independent DU-145 prostate cancer in vivo by luteinising hormone-releasing hormone antagonist Cetrolex and Bombesin antagonists RC-3940-II and RC-3950-II," European Journal of Cancer, 33(7): 1141-1148 (1997).

Mincheff, et al., "Naked DNA and Adenoviral Immunizations for Immunotherapy of Prostate Cancer: A Phase I/II Clinical Trial," Prostate Cancer: 38: 208-217 (2000).

Herbert Lepor, "The Role of Gonadotropin—Releasing Hormone Antagonists for the Treatment of Benign Prostatic Hyperplasia," Review in Urology, 8(4): 183-189 (2006).

Neal, et al., "Prostate Specific Antigen and Prostatis I. Effect of Prostatitis on Serum PSA in the Human and Nonhuman Primate," The Prostate, 20: 105-111 (1992).

Haupt, et al., "The Potential of DNA Vaccination against Tumor-Associated Antigens for Antitumor Therapy," Experimental Biological Medicine, 227(4): 227-237 (2002).

Lou, et al., "Immunogene Therapy of Tumors with a Vaccine Based on the Ligand-Binding Domain of Chicken Homologous Integrin $\beta_3$," Immunological Investigations, 31(1): 51-69 (2002).

Boyer, et al., "Protection of chimpanzees from high-dose heterologous HIV-1 challenge by DNA vaccination," Nature Medicine, 3(5): 526-532 (1997).

Wolchok, et al., "DNA Vaccines: An Active Immunization Strategy for Prostate Cancer," Seminars in Oncology, 30(5): 659-666 (2003).

Rabbani, et al. "Androgen Deprivation Therapy for Prostate Cancer: New Developments," Infections in Urology, 12(4): 104-121 (1999).

Wang, et al., "Prostate Antigen of Human Cancer Patients," Methods in Cancer Research, 19: 179-197 (1982).

Haviv, et al., "LHRH Antagonists," Integration of Pharmaceutical Discovery and Development, vol. 11, Plenum Publishing Corporation, 1998.

Gauthier, et al., "Characterization of rhesus monkey prostate specific antigen cDNA," Biochimica et Biophysica Acta, 1174: 207-210 (1993).

Boyer, et al., "In vivo protective anti-HIV immune response in non-human primates through DNA immunization," Journal of Medical Primatology, 25: 242-250 (1996).

PCT International Search Report dated Jul. 26, 2006.

* cited by examiner

Fig. 1

```
                                      -24
                                           Met Trp Val Leu Val Val Phe Leu Thr Leu Ser
      1    gctcaccgcctgcacctggacagctgtgtcacc ATG TGG GTT CTG GTT GTC TTC CTC ACC CTG TCC -1    1
           Val Thr Trp Ile Gly Ala Ala Pro Leu Ile Leu Ser Arg Ile Val Gly Gly Trp Glu Cys
     67    GTG ACG TGG ATT GGC GCT GCA CCC CTC ATC CTG TCT CGG ATT GTG GGA GGC TGG GAG TGC 20
           Glu Lys His Ser Gln Pro Trp Gln Val Leu Val Ala Ser His Gly Arg Ala Val Cys Gly
    127    GAG AAG CAT TCC CAA CCC TGG CAG GTG CTT GTG GCC TCT CAT GGC AGG GCA GTC TGC GGG 40
           Gly Val Leu Val His Pro Gln Trp Val Leu Thr Ala Ala His Cys Ile Arg Ser His Ser
    187    GGT GTT CTG GTG CAC CCC CAG TGG GTG CTC ACA GCT GCC CAC TGC ATC AGG AGC CAC AGC 60
           Val Ile Leu Leu Gly Arg His Asn Pro Tyr Tyr Pro Glu Asp Thr Gly Gln Val Phe Gln
    247    GTG ATC TTG CTG GGT CGG CAC AAC CCG TAT TAT CCT GAA GAC ACG GGC CAG GTG TTT CAG 80
           Val Ser His Ser Phe Pro His Pro Leu Tyr Asn Met Ser Leu Leu Lys Asn Arg Tyr Leu
    307    GTC AGC CAC AGC TTC CCA CAC CCG CTC TAC AAC ATG AGC CTC CTG AAG AAT CGA TAC CTC 100
           Gly Pro Gly Asp Asp Ser Ser His Asp Leu Met Leu Leu Arg Leu Ser Glu Pro Ala Glu
    367    GGG CCA GGT GAT GAC TCC AGC CAC GAC CTC ATG CTG CTC CGC CTG TCA GAG CCT GCC GAG 120
           Ile Thr Asp Ala Val Gln Val Leu Asp Leu Pro Thr Trp Glu Pro Glu Leu Gly Thr Thr
    427    ATC ACA GAT GCT GTG CAG GTC CTG GAC CTG CCC ACC TGG GAG CCA GAG CTG GGG ACC ACG 140
           Cys Tyr Ala Ser Gly Trp Gly Ser Ile Glu Pro Glu Glu His Leu Thr Pro Lys Lys Leu
    487    TGC TAC GCC TCA GGC TGG GGC AGC ATC GAA CCG GAG GAA CAC TTG ACT CCA AAG AAA CTT 160
           Gln Cys Val Asp Leu His Ile Ile Ser Asn Asp Val Cys Ala Gln Val His Ser Gln Lys
    547    CAG TGT GTG GAC CTC CAT ATT ATT TCC AAT GAT GTG TGT GCG CAA GTT CAC TCT CAG AAG 180
           Val Thr Lys Phe Met Leu Cys Ala Gly Ser Trp Met Gly Gly Lys Ser Thr Cys Ser Gly
    607    GTG ACC AAG TTC ATG CTG TGT GCT GGA AGC TGG ATG GGC GGC AAA AGC ACC TGC TCG GGT 200
           Asp Ser Gly Gly Pro Leu Val Cys Asp Gly Val Leu Gln Gly Ile Thr Ser Trp Gly Ser
    667    GAT TCT GGG GGC CCA CTG GTC TGT GAC GGT GTG CTT CAA GGT ATC ACG TCA TGG GGC AGT 220
           Gln Pro Cys Ala Leu Pro Arg Arg Pro Ser Leu Tyr Thr Lys Val Val Arg Tyr Arg Lys
    727    CAA CCA TGT GCC CTA CCC CGA AGG CCT TCC CTG TAC ACC AAG GTG GTG CGT TAC CGG AAG Trp Ile Gln Asp Thr Ile Met Ala Asn Pro ***
    787    TGG ATC CAG GAC ACC ATC ATG GCA AAC CCC TGA gcacccatcaactccctacttgtagcgaaaaaaa 856    aaatccacctcaagttctggcatcatttggctattctagacaccaggcacttggaaccttggaaatgaccgggccaagg
    936    ctcaagcctccccagttctattgacctttgtcctaaggtgtggggtccagggttgctaggaaaagaaatcagcagacac
   1016    aggtgtagaccagagtgtttcttaaatgggtgtaattttgtcctctccgtgtcctgggggacactggtcatgcctggag
```

Fig. 1 continued

```
1096  acatctcactcagtttctttgaggacccagataggttgggggtgtctgtgttgtttgtggggtacagagatgaaggagg
1176  ggtggggtccacactgagagagtagacagtgacacgtgctggatgctgtcctccactctgtcttggaggcactgggaag
1256  cctagagaaggctgcgaactgaggagggagggtcttcctgtggcatgggatggggatgaagtaaggagagggactggac
1336  tccctggaagctgattcaccatggggagaggtgtgtcaaggtcccccagacaaccctcagatttgatgatttcctagta
1416  gaactcacagaaataaagagctgttatactgtgaaaaaaaaaaaaaaaaaaaaaaaaaaa
```

Fig. 2

| | | |
|---|---|---|
| Human | -24 MWVPVVFLTLSVTWIGAAPLILSRIVGGWECEKHSQPWQVLVASR | 21 |
| Cyno | MWVLVVFLTLSVTWIGAAPLILSRIVGGWECEKHSQPWQVLVASH | |
| Rhesus | MWVLVVFLTLSVTWIGAAPLILSRIVGGWECEKHSQPWQVLVASR | |

| | |
|---|---|
| GRAVCGGVLVHPQWVLTAAHCIRNKSVILLGRHSLFHPEDTGQVFQVSHSFPHPLYD | 78 |
| GRAVCGGVLVHPQWVLTAAHCIRSHSVILLGRHNPYYPEDTGQVFQVSHSFPHPLYN | |
| GRAVCGGVLVHPQWVLTAAHCIRSNSVILLGRHNPYYPEDTGQVFQVSHSFPHPLYN | |

| | |
|---|---|
| MSLLKNRFLRPGDDSSHDLMLLRLSEPAELTDAVKVMDLPTQEPALGTTCYASGWGS | 135 |
| MSLLKNRYLGPGDDSSHDLMLLRLSEPAETTDAVQVLDLPTWEPELGTTCYASGWGS | |
| MSLLKNRYLGPGDDSSHDLMLLRLSEPAETTDAVQVLDLPTWEPELGTTCYASGQGS | |

| | |
|---|---|
| IEPEEFLTPKKLQCVDLHVISNDVCAQVHPQKVTKFMLCAGRWTGGKSTCSGDSGGP | 192 |
| IEPEEHLTPKKLQCVDLHIISNDVCAQVHSQKVTKFMLCAGSWMGGKSTCSGDSGGP | |
| IEPEEHLTPKKLQCVDLHIISNDVCAQVHSQKVTKFMLCAGSWMGGKSTCSGDSGGP | |

| | |
|---|---|
| LVCNGVLQGITSWGSEPCALPERPSLYTKVVHYRKWIKDTIVANP | 237 |
| LVCDGVLQGITSWGSQPCALPRRPSLYTKVVRYRKWIQDTIMANP | |
| LVCDGVLQGITSWGSQPCALPRRPSLYTKVVRYRKWIQDTIMANP | |

CYNOMOLGUS PROSTATE SPECIFIC ANTIGEN

CROSS-REFERENCE TO RELATED APPLICATIONS

This application is a divisional of U.S. application Ser. No. 11/138,242, filed 26 May 2005 now U.S. Pat. No. 7,342,107, currently allowed, which claims the benefit of U.S. Provisional Application No. 60/575,079, filed 27 May 2004, entitled, "Cynomolgus Prostate Specific Antigen." The entire contents of each of the foregoing applications is incorporated herein by reference.

FIELD OF THE INVENTION

The present invention relates to Cynomolgus monkey prostate specific antigen and its uses.

BACKGROUND OF THE INVENTION

Cancer is a serious disease that afflicts one in four people. In the last fifty years, there have been significant improvements in the early detection of cancer, as well as the development of a number of therapies to treat cancer. Therapies include surgery to remove primary tumors, and sublethal radiation and chemotherapy to treat disseminated disease. While these treatments have resulted in apparent cures for many patients, the treatments can be quite debilitating and are still often ineffective at preventing death from this disease.

Prostate cancer is the second leading cause of cancer-related death in men. Approximately 180,000 men will be diagnosed with prostate cancer each year and 40,000 succumb to the disease each year. Prostate tumor cells have a low proliferation rate and do not respond to standard chemotherapies, which are most toxic to the most rapidly dividing cells in the body. Instead, prostate cancer can be treated surgically, with radiation therapy or hormonal therapy. Surgery and radiation therapy can lead to undesirable side effects, such as incontinence and impotence. The disease can often be successfully managed with hormonal therapy, which starves the tumor cells for required growth factors. However, eventually all tumors treated in this way become androgen-independent and there is no effective treatment beyond that point.

Treatment of cancer with active immunotherapy has shown promise in many preclinical models, and in a few clinical trials as an alternative or adjunct to surgery, radiation or chemotherapy. The goal of active immunotherapy is to create a therapeutic immune response against tumor-specific antigens, which then targets tumor cells for destruction. However, most tumor antigens are self-antigens, to which the patient is tolerant. Indeed, central and peripheral tolerance mechanisms are expected to hamper the generation of effective immunity against tumors that express self-antigens.

One way to solve the problem of how to break tolerance against a given self-antigen is to use a closely related gene or protein from a different species as an immunogen. This type of immunization is also known as xenogeneic immunization and its potency lies in either the random creation of heteroclitic epitopes in the xenogeneic sequences with enhanced binding capacity to MHC class I antigens and/or the presence of strong helper epitopes within the xenogeneic sequence. For example, injection of plasmid DNA encoding a xenogeneic differentiation antigen is a powerful means to induce antibody and T-cell responses to otherwise poorly immunogenic self-antigens. This xenogeneic approach has been shown to work for a variety of cancer models using mouse or rat sequences by inducing active immunity to several different types of genes, including angiogenesis genes (Liu et al., *Blood* 102:1815-23, 2003), membrane glycoproteins (Wolchok et al., *Cancer Immun.* 1, 9-18 (2001); Sioud and Sorensen D., *Eur. J. Immunol.* 33, 38-45 (2003)), and integrins (Lou et al., *Immunol. Invest.* 31, 51-69 (2002)).

Prostate tumors and some breast malignancies express prostate specific antigen (PSA), also known as kallikrein 3 (KLK3), on their surface. PSA is well known as a serum marker for prostate cancer; increasing serum levels of PSA typically correlate well with the severity of the disease. It is unclear if PSA has a role in the etiology of prostate cancer; various reports have indicated that PSA could either enhance or inhibit tumorigenicity. Several cytotoxic T-lymphocyte (CTL) epitopes for PSA have been described for the HLA A2 and A3 haplotypes; identification of these epitopes support the possibility of generating therapeutic in vivo CTL by vaccination.

In fact, use of DNA encoding human and mouse prostate-specific membrane antigen (PSMA) has been tested in phase I clinical trials in patients with recurrent prostate cancer. See Wolchok et al., *Semin. Oncol.* 30, 659-66 (2003). These authors have also shown in pre-clinical studies that use of xenogeneic DNA (e.g., injection of human PSMA DNA into mice) is an absolute requirement to overcome immunologic tolerance. However, a need still exists to improve current vaccine strategies by treating human disease with a more closely related PSA antigen to stimulate anti-PSA immunity by xenogeneic immunization.

BRIEF DESCRIPTION OF THE DRAWING

FIG. 1 shows the nucleotide and deduced amino acid sequence of full-length Cynomolgus monkey PSA.

FIG. 2 shows an amino acid sequence comparison of Cynomolgus monkey, Human and Rhesus monkey PSA.

SUMMARY OF THE INVENTION

One aspect of the invention is an isolated polynucleotide comprising a polynucleotide having the sequence shown in SEQ ID NO: 1 or a complementary sequence, fragment or variant thereof.

Another aspect of the invention is an isolated polynucleotide comprising a polynucleotide having the sequence shown in SEQ ID NO: 2 or a complementary sequence, fragment or variant thereof.

Another aspect of the invention is an isolated polynucleotide comprising a polynucleotide having the sequence shown in SEQ ID NO: 4 or a complementary sequence, fragment or variant thereof.

Another aspect of the invention is an isolated polynucleotide comprising a polynucleotide encoding the amino acid sequence shown in SEQ ID NO: 3 or a complementary sequence, fragment or variant thereof.

Another aspect of the invention is an isolated polynucleotide comprising a polynucleotide encoding the amino acid sequence shown in SEQ ID NO: 5 or a complementary sequence, fragment or variant thereof.

Another aspect of the invention is an isolated polypeptide comprising a polypeptide having the sequence shown in SEQ ID NO: 3.

Another aspect of the invention is an isolated polypeptide comprising a polypeptide having the sequence shown in SEQ ID NO: 5.

Another aspect of the invention is an isolated full-length human prostate specific antigen consisting of the amino acid sequence shown in SEQ ID NO: 3.

Another aspect of the invention is an isolated mature human PSA consisting of the amino acid sequence shown in SEQ ID NO: 5.

DETAILED DESCRIPTION OF THE INVENTION

All publications, including but not limited to patents and patent applications, cited in this specification are herein incorporated by reference as though fully set forth.

As used herein, the term "DNA vaccines" or "nucleic acid vaccines" denotes compositions useful for the direct in vivo introduction of DNA encoding an antigen into tissues of a subject for expression of the antigen by tissue cells. DNA vaccines are described in, e.g., International Patent Publications WO 95/20660 and WO 93/19183.

As used herein, the term "nucleic acid adjuvant" means a nucleotide sequence coding for a protein or protein fragment that enhances an immune response to an antigen.

The present invention provides isolated Cynomolgus monkey (*Macaca fascicularis*) PSA polypeptides and polynucleotides. The invention also provides a full-length Cynomolgus monkey PSA having the amino acid sequence set forth in SEQ ID NO: 3 and the polynucleotide encoding it including, but not limited to, the polynucleotide having the sequence set forth in SEQ ID NO: 1 or 2 or their complementary sequences. Full-length Cynomolgus PSA is predicted to have a 24 residue N-terminal leader sequence (SEQ ID NO: 6). The invention also provides a mature Cynomolgus monkey PSA lacking the leader sequence and having the amino acid sequence set forth in SEQ ID NO: 5 and the polynucleotide encoding it including but not limited to, the polynucleotide having the sequence set forth in SEQ ID NO: 4 or its complementary sequences. The invention further provides for equivalent fragments and variants of Cynomolgus monkey PSA, as well as encoding or complementary nucleic acids, vectors comprising a Cynomolgus monkey PSA or fragments or variants, host cells containing such vectors and methods of making and methods of use of such Cynomolgus PSA, vectors or host cells.

A "fragment" is a polypeptide having an amino acid sequence that is part of but not all of any amino acid sequence of any polypeptide of the invention where the fragment contains residues 70 and/or 79 of the full-length form (equivalent to residues 21 and/or 46 of the mature form). Fragments can include, e.g., truncation polypeptides having a portion of an amino acid sequence as shown in amino acid sequence shown in SEQ ID NO: 3 or 5, or of variants thereof, such as a continuous series of residues that includes a heterologous amino- and/or carboxy-terminal amino acid sequence. Degradation forms of the polypeptides of the invention produced by or in a host cell are also included. Other exemplary fragments are characterized by structural or functional attributes such as fragments that comprise alpha-helix or alpha-helix forming regions, beta-sheet or beta-sheet forming regions, turn or turn-forming regions, coil or coil-forming regions, hydrophilic regions, hydrophobic regions, alpha-amphipathic regions, beta-amphipathic regions, flexible regions, surface-forming regions, substrate binding regions, extracellular regions and high antigenic index regions.

Specific exemplary fragments include residues 141 to 163 of the mature form that encode peptides that can bind human Class I molecules. See Correale et al., *J. Natl. Cancer Inst.* 89, 293-300 (1997) and Xue et al., *The Prostate* 30, 73-78 (1997). Other exemplary fragments include residues 16-25, 42-50, 48-56 and 75-83. Further exemplary fragments include an isolated polypeptide comprising an amino acid sequence having at least 10, 15, 20, 30, 40, 50 or 100 contiguous amino acids from the amino acid sequence set forth in SEQ ID NO: 3 where the fragment contains residues 45 and/or 70 of the full-length form, or an isolated polypeptide comprising an amino acid sequence having at least 10, 15, 20, 30, 40, 50 or 100 contiguous amino acids from the amino acid sequence set forth in SEQ ID NO: 5 where the fragment contains residues 21 and/or 46 of the mature form.

A "variant" polypeptide is a Cynomolgus PSA polypeptide or fragment in which amino acid substitutions, insertions, deletions or combinations thereof have been made. Naturally occurring, modified or atypical amino acids can be used for substitutions and insertions. A variant polynucleotide is a polynucleotide encoding variant polypeptides. Variant polypeptides of the invention elicit an immune response to PSA in a host.

The polynucleotides of the invention are useful for preparing a composition having an isolated polynucleotide encoding an antigenic determinant of Cynomolgus monkey PSA and a promoter controlling expression of the polynucleotide. The composition can further include an isolated polynucleotide encoding a nucleic acid adjuvant such as interleukin-18 (IL-18) and a promoter polynucleotide controlling expression of the IL-18. These compositions can be used to elicit an immune response to a cancer-associated tumor protein in a mammal and are useful as nucleic acid vaccines for the treatment and/or prophylaxis of certain cancers or other tumor-related pathologies.

Antigenic determinants useful in the invention are obtained or derived from Cynomolgus monkey PSA. The tumor antigens could also be mutated to enhance their immunogenicity. Examples of how the antigen genes could be modified to effect a more robust immune response to the antigen protein include changes that affect antigen gene expression levels, such as addition of intron sequences, alteration or removal of signal sequences required for secretion or optimization of codons for improved translation. In addition, the antigen gene could be modified to introduce changes to the translated product of the gene, such as addition of ubiquitination signals for degradation, addition of subcellular compartment targeting sequences, addition of molecular chaperone sequences, and optimization of CTL epitope sequences. The antigen genes could be fused together to increase immunogenicity. The CTL/helper epitopes could be linked together, or inserted as part of another molecule, such as an immunoglobulin molecule. Nucleotides encoding at least one antigenic determinant of the molecules disclosed above are useful in the invention. Further, sequences complementary to any of the polynucleotides disclosed above are also useful in the compositions of the invention.

Compositions of the invention including these antigenic determinants are useful for the treatment of any cancer where PSA is uniquely expressed, over-expressed or associated with the presence of tumors caused by the cancer. These cancers include, but are not limited to, prostate, including hormone-refractory prostate cancer (HRPC), and breast cancer.

The invention also provides a mature polypeptide coding sequence or a fragment thereof in reading frame with another coding sequence produced synthetically or derived from another species, such as a sequence encoding a leader or secretory sequence, a pre- or pro- or prepro-protein sequence. The polynucleotides of the invention may also contain at least one non-coding sequence, such as transcribed but not translated sequences, termination signals, ribosome binding sites, mRNA stabilizing sequences, introns and polyadenylation signals. The polynucleotide sequences may also contain additional sequences encoding additional amino acids. These additional polynucleotide sequences may, for example, encode a marker sequence such as a hexa-histidine peptide, as described in Gentz et al., *Proc. Natl. Acad. Sci. (USA)* 86, 821-824 (1989) or the HA peptide tag as described in Wilson et al., *Cell* 37, 767 (1984) which facilitate the purification of fused polypeptides.

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production of the polypeptides of the invention, host cells can be genetically engineered to incorporate expression systems or portions thereof and polynucleotides of the invention. Introduction of a polynucleotide into a host cell can be effected by methods well known to those skilled in the art from laboratory manuals such as Davis et al., *Basic Methods in Molecular Biology*, $2^{nd}$ ed., Appleton & Lange, Norwalk, Conn. (1994) and Sambrook et al., *Molecular Cloning: A Laboratory Manual*, $3^{rd}$ ed., Cold Spring Harbor Laboratory Press, Cold Spring Harbor, N.Y. (2001). These methods include calcium phosphate transfection, DEAE-Dextran mediated transfection, microinjection, cationic lipid-mediated transfection, electroporation, transduction, scrape loading, ballistic introduction and infection.

Representative examples of hosts include Archaea cells; bacterial cells such as streptococci, staphylococci, enterococci, *E. coli*, streptomyces, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells.

A great variety of expression systems can be used to produce the polypeptides of the invention. Such systems include chromosomal-, episomal- and virus-derived vectors such as vectors derived from bacterial plasmids, bacteriophage, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids. The expression system constructs may contain control regions that regulate or cause expression. Generally, any system or vector suitable to maintain or propagate polynucleotides and/or to express polypeptides in a host may be used for expression. An appropriate DNA sequence may be inserted into the expression system by any of a variety of techniques well known to those skilled in the art, such as, e.g., those set forth in Sambrook et al., supra.

In eukaryotic expression systems, polypeptides of the invention can be secreted into the lumen of the endoplasmic reticulum or extracellular environment by inclusion of appropriate secretion signals such as a signal peptide or leader sequence. These signals may be heterologous or endogenous to Cynomolgus PSA such as the signal sequence having the amino acid sequence shown in SEQ ID NO: 6 (predicted).

The polypeptides of the present invention may also be produced by chemical synthesis such as solid phase peptide synthesis on an automated peptide synthesizer, using known amino acid sequences or amino acid sequences derived from the DNA sequence of the polynucleotides of the invention. Such techniques are well known to those skilled in the art.

Polypeptides of the invention can be recovered and purified from recombinant cell cultures by well-known methods including ammonium sulfate or ethanol precipitation, acid extraction, high-performance liquid chromatography, anion or cation exchange chromatography, phosphocellulose chromatography, hydrophobic interaction chromatography, affinity chromatography, hydroxyapatite chromatography and lectin chromatography. Well-known techniques for refolding protein may be employed to regenerate an active conformation when the protein is denatured during isolation and/or purification.

The polynucleotides and polypeptides of the invention comprising at least one epitope of Cynomolgus PSA can be used to produce polyclonal or monoclonal antibodies. Techniques for making murine, chimeric, humanized and fully human monoclonal antibodies using protein or nucleic acid immunization are known to those skilled in the art.

The polynucleotides and polypeptides of the invention are also useful for assaying a medium for the presence of a substance that modulates PSA protein function by affecting the binding of a Cynomolgus PSA protein to serum proteins. Examples of modulators include polypeptides or small organic molecules.

For use as DNA vaccines, the polypeptides of the invention could be contained within one or more cellular delivery vectors such as plasmids, mammalian viruses, bacteria or mammalian cells having appropriate regulatory and control elements as are well known to those skilled in the art. For example, expression of the tumor antigen and nucleic acid adjuvant polynucleotide sequences could be under the control of a suitable promoter such as the human cytomegalovirus immediate early (HCMV IE) promoter or dihydrofolate reductase promoter, and a polyadenylation (polyA) signal such as the SV40 late, SV40 early polyA signal or a synthetic polyA sequence. An intron may be included for enhanced expression, such as the HCMV IE intron A or natural introns from the antigen or adjuvant genes.

An exemplary plasmid useful with the polypeptides of the invention contains an *E. coli* origin of replication, an aph(3')-1a kanamycin resistance gene, HCMV immediate early promoter with intron A, a synthetic polyA sequence and a bovine growth hormone terminator. Another exemplary plasmid contains an *E. coli* origin of replication, an ant(4')-1a kanamycin resistance gene, Rous sarcoma virus long terminal repeat sequences, HCMV immediate early promoter and an SV40 late polyA sequence.

Examples of suitable viruses that can act as recombinant viral hosts for the polypeptides of the invention include vaccinia, canarypox, and adenovirus, as are known in the art. Various genetically engineered virus hosts ("recombinant viruses") can also be used. Viral cellular delivery vectors containing the compositions of the invention can promote a suitable immune response that targets activation of B lymphocytes, helper T lymphocytes, and cytotoxic T lymphocytes.

A preferred recombinant virus for use with the compositions of the invention is vaccinia virus (International Patent Publication WO 87/06262; Cooney et al., *Proc. Natl. Acad. Sci. USA* 90, 1882-1886 (1993); Graham et al., *J. Infect. Dis.* 166, 244-252 (1992); McElrath et al., *J. Infect. Dis.* 169, 41-47 (1994)). In another embodiment, recombinant canarypox can be used (Pialoux et al., *AIDS Res. Hum. Retroviruses* 11, 373-381 (1995), erratum in *AIDS Res. Hum. Retroviruses* 11, 875 (1995); Andersson et al., *J. Infect. Dis.* 174, 977-985 (1996); Fries et al., *Vaccine* 14, 428-434 (1996); Gonczol et al., *Vaccine* 13, 1080-1085 (1995)). Another alternative is defective adenovirus or adeno-associated viruses or retroviruses (Gilardi-Hebenstreit et al., *J. Gen. Virol.* 71, 2425-2431 (1990); Prevec et al., *J. Infect. Dis.* 161, 27-30 (1990); Lubeck et al., *Proc. Natl. Acad. Sci. USA* 86, 6763-6767 (1989); Xiang et al., *Virology* 219, 220-227 (1996)). Other suitable viral vectors include attenuated or defective DNA virus, such as but not limited to herpes simplex virus (HSV) (see, e.g., Kaplitt et al., *Molec. Cell. Neurosci.* 2, 320-330 (1991)), papillomavirus, Epstein Barr virus (EBV), see, e.g., U.S. Pat. Nos. 5,990,091; 5,766,599; 5,756,103; 6,086,890; 6,274,147; 5,585,254; 6,140,114; 5,616,326; 6,099,847; 6,221,136; 6,086,891; 5,958,425; 5,744,143; 5,558,860; 5,266,489; 5,858,368; 5,795,872; 5,693,530; 6,020,172.

The polypeptides of the invention can be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the polypeptides of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected. Further, plasmids containing the polypeptides of the invention could also be formulated in microparticles or with lipid, buffer or other excipients.

The polypeptides of the invention can also be formulated with adjuvants that could aid delivery of DNA, maintain its integrity in vivo or enhance the immunogenicity of the vaccine. Chemical adjuvants can include compounds or mixtures that enhances the immune response to an antigen. A chemical adjuvant can serve as a tissue depot that slowly releases the antigen and also as a lymphoid system activator that non-specifically enhances the immune response (Hood et al., *Immunology*, 2nd ed., (1984), Benjamin/Cummings, Menlo Park, Calif., p. 384). Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and useful human adjuvants such as BCG (*Bacillus* Calmette-Guerin) and *Corynebacterium parvum*. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). In a specific embodiment, compositions of the invention are administered intramuscularly in alum. Alternatively, the compositions of the invention can be administered subcutaneously, intradermally, intraperitoneally, intramuscularly or via other acceptable vaccine administration routes.

The polypeptides of the invention can be temporally administered in different orders or administered in different places in the body at the same time. The polypeptides of the invention could also be delivered by direct injection into muscle, skin, lymph node, or by application to mucosal surfaces. In a specific embodiment, polypeptides of the invention are provided intramuscularly. Other potential modes of delivery would include injection of DNA, followed by electroporation to enhance cellular uptake and expression of DNA or administration by a gene gun or a similar device. For screening anti-tumor activity of sera or cells from an individual immunized with a polypeptide of the invention, any suitable screening assay can be used, as is known in the art.

The polypeptides of the invention, when in a pharmaceutical preparation, can be present in unit dose forms. The appropriate therapeutically effective dose can be determined readily by those of skill in the art. A determined dose may, if necessary, be repeated at appropriate time intervals selected as appropriate by a physician during the treatment period.

The polypeptides of the invention can be lyophilized for storage and reconstituted in a suitable carrier prior to use. This technique has been shown to be effective with conventional protein preparations and art-known lyophilization and reconstitution techniques can be employed.

The present invention will now be described with reference to the following specific, non-limiting examples.

EXAMPLE 1

Isolation, Cloning and Sequencing of Cynomolgus Monkey PSA Gene

RNA was purified from Cynomolgus prostate tissue (Cambrex Bio Science Walkersville Inc, Walkersville, Md.) using Trizol reagent (Invitrogen, Carlsbad, Calif.) according to the manufacturer's instructions. Reverse transcription reactions were carried out using Superscript II Reverse Transcriptase kit and were primed using an oligo dT primer. For polymerase chain reaction (PCR), a gene-specific forward primer that annealed to the translation initiation site was paired with a reverse primer that annealed to conserved regions within the 3' untranslated regions of the Human and Rhesus PSA mRNAs (SEQ ID NOs: 11 and 12, Table 1, 5' PSA and 3' PSA). The first ATG is located at residues 19-21 of the 5' PSA primer shown in Table 1. The 5' PSA primer anneals to the translation initiation site with a Bam HI site (underlined in Table 1) engineered on the 5' end and the 3' PSA primer anneals to a conserved region within the 3' untranslated region with a Bam HI site engineered on the 3' end. PCR was performed using 100 ng of each primer with 100 ng cDNA template under the following conditions: 30 cycles of 94° C. 30 seconds, 60° C. 1 minute, 68° C. 1 minute, followed by one cycle of 68° C. for 5 minutes. Ten percent of the PCR reactions were analyzed on agarose gels, and revealed a band of approximately 1000 bp (data not shown). PCR products were purified using Qiaquick PCR purification (Qiagen, Valencia, Calif.). Approximately 60 ng of each product was directly sequenced using the Big Dye Terminator Cycle Sequencing Kit (PE Applied Biosystems, Foster City, Calif.), followed by analysis on a Prism ABI377 automated DNA sequencing apparatus. PCR fragments were sequenced using 20 ng of 5' PSA seq and 3' PSA seq primers corresponding to nucleotides 383-406 and 653-676, respectively (SEQ ID NOs: 13 and 14, Table 1). In addition, specific PCR products were also subcloned and sequenced. All PSA gene results were confirmed from prostate tissue from at least two Cynomolgus monkeys.

The sequences of the fragments were compared using Vector NTi software (Invitrogen, Frederick, Md.) to the Genbank database and aligned with Human and Rhesus PSA sequences (Genbank accession #M21896 and #X73560, respectively). The cynomolgus PSA sequence was also BLAST searched against available embl and other sequence databases. BLASTP, TBLASTN and BLASTN searches were performed and no identical records were found.

To obtain the complete sequence of the 5' and 3' untranslated regions of the cynomolgus PSA gene, rapid amplification of cDNA ends (RACE) was employed. Total RNA was extracted from the prostates of at least two adult male Cynomolgus monkeys and the 5' and 3' untranslated regions of the mRNA transcript was amplified by ligase-mediated RACE reactions using the 5' and 3' RACE primers shown in Table 1 corresponding to nucleotides 49-72 and 782-805, respectively (SEQ ID NOs: 15 and 16).

TABLE 1

Cynomolgus PSA gene cloning and sequencing oligonucleotides.

| Name | Sequence |
|---|---|
| 5' PSA | 5'-CTGGATCCCTGTGCCACCATGTGG-3' (SEQ ID NO: 11) |
| 3' PSA | 5'-CCGGATCCTGCTGATTTCTTTTCC-3' (SEQ ID NO: 12) |
| 5' PSA seq | 5'-CCAGCCACGACCTCATGCTGCTCC-3' (SEQ ID NO: 13) |
| 3' PSA seq | 5'-CCCCAGAATCACCCGACAGGTGC-3' (SEQ ID NO: 14) |
| 5' PACE | 5'-CGTCACGGACAGGGTGAGGAAGAC-3' (SEQ ID NO: 15) |
| 3' PACE | 5'-GGAAGTGGAGCCAGGACACCATCA-3' (SEQ ID NO: 16) |

Four clones from three different monkeys were sequenced and aligned. The nucleotide and deduced amino acid sequence of full-length Cynomolgus monkey PSA cDNA is shown in FIG. 1 and SEQ ID NOs: 1 and 2. In FIG. 1, the translated amino acid sequences of the coding region are numbered and shown above the nucleotide sequence. The nucleotide residues are numbered on the left. The putative polyadenylation signal is in bold type.

Sequencing analysis of the cDNA fragments showed that the Cynomolgus PSA mRNA consists of a short 5' noncoding region of about 33 bases (residues 1 to 33 of SEQ ID NO: 1), an open reading frame of 783 bases (residues 34 to 816 of SEQ ID NO: 1), corresponding to 261 amino acids (SEQ ID NO: 3) and a 3' untranslated region of 660 bases (residues 817 to 1476 of SEQ ID NO: 1). The first 24 amino acids of Cynomolgus PSA are expected to include the signal sequence (SEQ ID NO: 6). The amino terminus of mature PSA is predicted to be the isoleucine shown as residue 1 in FIG. 1. The polynucleotide sequence and amino acid sequence of the mature 237 amino acid form of Cynomolgus PSA is shown in SEQ ID NOs: 4 and 5, respectively.

EXAMPLE 2

Sequence Comparisons of Primate PSA Genes

Protein sequence comparisons of the Cynomolgus PSA sequence to the Genbank database of Human and Rhesus PSA cDNAs are shown in FIG. 2. Residues that differ between the species are shown in bold and highlighted. Each species encodes a mature protein predicted to be 237 amino acids in length. The comparisons revealed that the Cynomolgus PSA amino acid sequence was 89.7% identical to Human PSA (27/261 residue differences) (FIG. 2). The Rhesus amino acid sequence was 90% identical to the human gene (26/261 residue differences). The Cynomolgus and Rhesus amino acid sequences differed at only two amino acids, namely residues 21 and 46 of the mature form, for 99.2% identity.

The nucleotide sequences of the three genes were also compared for the coding region. There is approximately 93.5% identity between Human and the Cynomolgus and Rhesus sequences (data not shown). Only three nucleotide residues differ in this region between the two primate cDNAs, giving 99.6% identity. Like the Human and Rhesus proteins, Cynomolgus PSA also has a serine at position 183, which has been shown to be responsible for the cleavage specificity of the serine proteases at hydrophobic amino acids (Lundwall, A. and Lilja, H. *FEBS Letters* 214, 317-322 (1987)).

The 5' untranslated regions (UTR) were identical between Rhesus and Cynomolgus monkeys. The sequence of the Cynomolgus 5' UTR was eight bases longer than the human sequence (data not shown).

There were several differences in the 3' UTRs between the species. First, the Cynomolgus 3' UTR is 75 bases shorter than the rhesus 3'UTR with a 72 base pair deletion located at bases 405/406 from the TGA stop codon of the Cynomolgus sequence. Besides these deletions, there are only three nucleotide differences in the 3'UTR between the species. As expected, there were more differences between the Human and Cynomolgus 3'UTR. First, there is a 54 base pair deletion in the human sequence corresponding to bp 34-87 of the Cynomolgus sequence. In addition, there are 4 base pair additions in the Cynomolgus sequence and one base pair deletion in addition to the 72 base pair deletion compared to the human sequence. There are also 31 base pair differences between the species (data not shown).

EXAMPLE 3

Analysis of PSA Expression in Cynomolgus Tissues

To investigate the RNA expression pattern of Cynomolgus PSA in Cynomolgus tissues, RT-PCR analysis was performed using RNA purified from different tissues. Total RNA from the kidney, lung, testis, thymus and prostate was isolated and cDNA was synthesized as described in Example 1. No DNA template was used as a negative control for non-specific amplification. Isolated total RNA was used as a template for first strand cDNA synthesis using Superscript II reverse transcriptase and an oligo dT primer. 100 ng of cDNA was subjected to PCR amplification as described above. The PSA gene was amplified using the 5' PSA (SEQ ID NO: 11) and 3' PSA (SEQ ID NO: 12) primers to yield a 1000 bp PSA-specific product. β-actin was amplified as a loading control using Cynomolgus-specific forward (SEQ ID NO: 17) and reverse (SEQ ID NO: 18) primers; a 216 bp product was amplified. The results indicated that PSA mRNA was only detected in the prostate tissue and not in the kidney, lung, testis or thymus (data not shown).

The present invention now being fully described, it will be apparent to one of ordinary skill in the art that many changes and modifications can be made thereto without departing from the spirit or scope of the appended claims.

SEQUENCE LISTING

<160> NUMBER OF SEQ ID NOS: 18

<210> SEQ ID NO 1
<211> LENGTH: 1467
<212> TYPE: DNA
<213> ORGANISM: Macaca fascicularis

<400> SEQUENCE: 1

```
gctcaccgcc tgcacctgga cagctgtgtc accatgtggg ttctggttgt cttcctcacc        60
ctgtccgtga cgtggattgg cgctgcaccc ctcatcctgt ctcggattgt gggaggctgg       120
gagtgcgaga agcattccca accctggcag gtgcttgtgg cctctcatgg cagggcagtc       180
tgcgggggtg ttctggtgca cccccagtgg gtgctcacag ctgcccactg catcaggagc       240
cacagcgtga tcttgctggg tcggcacaac ccgtattatc tgaagacac gggccaggtg        300
tttcaggtca gccacagctt cccacacccg ctctacaaca tgagcctcct gaagaatcga       360
tacctcgggc caggtgatga ctccagccac gacctcatgc tgctccgcct gtcagagcct       420
gccgagatca cagatgctgt gcaggtcctg gacctgccca cctgggagcc agagctgggg       480
accacgtgct acgcctcagg ctggggcagc atcgaaccgg aggaacactt gactccaaag       540
aaacttcagt gtgtggacct ccatattatt tccaatgatg tgtgtgcgca agttcactct       600
cagaaggtga ccaagttcat gctgtgtgct ggaagctgga tgggcggcaa aagcacctgc       660
tcgggtgatt ctgggggccc actggtctgt gacggtgtgc ttcaaggtat cacgtcatgg       720
ggcagtcaac catgtgccct accccgaagg ccttccctgt acaccaaggt ggtgcgttac       780
cggaagtgga tccaggacac catcatggca aaccccgagg cacccccatca actccctact       840
tgtagcgaaa aaaaaatcc acctcaagtt ctggcatcat ttggctattc tagacaccag        900
gcacttggaa ccttggaaat gaccgggcca aggctcaagc ctccccagtt ctattgacct       960
ttgtcctaag gtgtggggtc cagggttgct aggaaaagaa atcagcagac acaggtgtag      1020
accagagtgt ttcttaaatg ggtgtaattt tgtcctctcc gtgtcctggg ggacactggt      1080
catgcctgga gacatctcac tcagtttctt tgaggaccca gataggttgg gggtgtctgt      1140
gttgtttgtg gggtacagag atgaaggagg ggtggggtcc acactgagag agtagacagt      1200
gacacgtgct ggatgctgtc ctccactctg tcttggaggc actgggaagc ctagagaagg      1260
ctgcgaactg aggagggagg gtcttcctgt ggcatgggat ggggatgaag taaggagagg      1320
gactggactc cctggaagct gattcaccat ggggagaggt gtgtcaaggt cccccagaca      1380
accctcagat ttgatgattt cctagtagaa ctcacagaaa taaagagctg ttatactgtg      1440
aaaaaaaaaa aaaaaaaaaa aaaaaaa                                          1467
```

<210> SEQ ID NO 2
<211> LENGTH: 783
<212> TYPE: DNA
<213> ORGANISM: Macaca fascicularis

<400> SEQUENCE: 2

```
atgtgggttc tggttgtctt cctcaccctg tccgtgacgt ggattggcgc tgcacccctc        60
atcctgtctc ggattgtggg aggctgggag tgcgagaagc attcccaacc ctggcaggtg       120
cttgtggcct ctcatggcag ggcagtctgc gggggtgttc tggtgcaccc ccagtgggtg       180
ctcacagctg cccactgcat caggagccac agcgtgatct tgctgggtcg gcacaacccg       240
tattatcctg aagacacggg ccaggtgttt caggtcagcc acagcttccc acacccgctc       300
```

-continued

```
tacaacatga gcctcctgaa gaatcgatac ctcgggccag gtgatgactc cagccacgac    360
ctcatgctgc tccgcctgtc agagcctgcc gagatcacag atgctgtgca ggtcctggac    420
ctgcccacct gggagccaga gctggggacc acgtgctacg cctcaggctg gggcagcatc    480
gaaccggagg aacacttgac tccaaagaaa cttcagtgtg tggacctcca tattatttcc    540
aatgatgtgt gtgcgcaagt tcactctcag aaggtgacca agttcatgct gtgtgctgga    600
agctggatgg gcggcaaaag cacctgctcg ggtgattctg ggggcccact ggtctgtgac    660
ggtgtgcttc aaggtatcac gtcatggggc agtcaaccat gtgccctacc ccgaaggcct    720
tccctgtaca ccaaggtggt gcgttaccgg aagtggatcc aggacaccat catggcaaac    780
ccc                                                                   783
```

<210> SEQ ID NO 3
<211> LENGTH: 261
<212> TYPE: PRT
<213> ORGANISM: Macaca fascicularis

<400> SEQUENCE: 3

```
Met Trp Val Leu Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser His Gly Arg Ala
        35                  40                  45

Val Cys Gly Gly Val Leu Val His Pro Gln Trp Val Leu Thr Ala Ala
    50                  55                  60

His Cys Ile Arg Ser His Ser Val Ile Leu Leu Gly Arg His Asn Pro
65                  70                  75                  80

Tyr Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
            100                 105                 110

Pro Gly Asp Asp Ser Ser His Asp Leu Met Leu Leu Arg Leu Ser Glu
        115                 120                 125

Pro Ala Glu Ile Thr Asp Ala Val Gln Val Leu Asp Leu Pro Thr Trp
    130                 135                 140

Glu Pro Glu Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Ile Ile Ser Asn Asp Val Cys Ala Gln Val His Ser Gln Lys Val
            180                 185                 190

Thr Lys Phe Met Leu Cys Ala Gly Ser Trp Met Gly Gly Lys Ser Thr
        195                 200                 205

Cys Ser Gly Asp Ser Gly Gly Pro Leu Val Cys Asp Gly Val Leu Gln
    210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Met Ala Asn Pro
            260
```

<210> SEQ ID NO 4
<211> LENGTH: 711
<212> TYPE: DNA
<213> ORGANISM: Macaca fascicularis

<400> SEQUENCE: 4

```
attgtgggag gctgggagtg cgagaagcat tcccaaccct ggcaggtgct tgtggcctct      60
catggcaggg cagtctgcgg gggtgttctg gtgcaccccc agtgggtgct cacagctgcc     120
cactgcatca ggagccacag cgtgatcttg ctgggtcggc acaacccgta ttatcctgaa     180
gacacgggcc aggtgtttca ggtcagccac agcttccac  acccgctcta caacatgagc     240
ctcctgaaga atcgatacct cgggccaggt gatgactcca gccacgacct catgctgctc     300
cgcctgtcag agcctgccga gatcacagat gctgtgcagg tcctggacct gcccacctgg     360
gagccagagc tggggaccac gtgctacgcc tcaggctggg gcagcatcga accggaggaa     420
cacttgactc caaagaaact tcagtgtgtg gacctccata ttatttccaa tgatgtgtgt     480
gcgcaagttc actctcagaa ggtgaccaag ttcatgctgt gtgctggaag ctggatgggc     540
ggcaaaagca cctgctcggg tgattctggg ggcccactgg tctgtgacgg tgtgcttcaa     600
ggtatcacgt catgggcag tcaaccatgt gccctacccc gaaggccttc cctgtacacc      660
aaggtggtgc gttaccggaa gtggatccag gacaccatca tggcaaaccc c              711
```

<210> SEQ ID NO 5
<211> LENGTH: 237
<212> TYPE: PRT
<213> ORGANISM: Macaca fascicularis

<400> SEQUENCE: 5

```
Ile Val Gly Gly Trp Glu Cys Glu Lys His Ser Gln Pro Trp Gln Val
1               5                   10                  15

Leu Val Ala Ser His Gly Arg Ala Val Cys Gly Gly Val Leu Val His
            20                  25                  30

Pro Gln Trp Val Leu Thr Ala Ala His Cys Ile Arg Ser His Ser Val
        35                  40                  45

Ile Leu Leu Gly Arg His Asn Pro Tyr Tyr Pro Glu Asp Thr Gly Gln
    50                  55                  60

Val Phe Gln Val Ser His Ser Phe Pro His Pro Leu Tyr Asn Met Ser
65                  70                  75                  80

Leu Leu Lys Asn Arg Tyr Leu Gly Pro Gly Asp Asp Ser Ser His Asp
                85                  90                  95

Leu Met Leu Leu Arg Leu Ser Glu Pro Ala Glu Ile Thr Asp Ala Val
            100                 105                 110

Gln Val Leu Asp Leu Pro Thr Trp Glu Pro Glu Leu Gly Thr Thr Cys
        115                 120                 125

Tyr Ala Ser Gly Trp Gly Ser Ile Glu Pro Glu Glu His Leu Thr Pro
    130                 135                 140

Lys Lys Leu Gln Cys Val Asp Leu His Ile Ile Ser Asn Asp Val Cys
145                 150                 155                 160

Ala Gln Val His Ser Gln Lys Val Thr Lys Phe Met Leu Cys Ala Gly
                165                 170                 175

Ser Trp Met Gly Gly Lys Ser Thr Cys Ser Gly Asp Ser Gly Gly Pro
            180                 185                 190

Leu Val Cys Asp Gly Val Leu Gln Gly Ile Thr Ser Trp Gly Ser Gln
        195                 200                 205

Pro Cys Ala Leu Pro Arg Arg Pro Ser Leu Tyr Thr Lys Val Val Arg
```

```
                210                 215                 220
Tyr Arg Lys Trp Ile Gln Asp Thr Ile Met Ala Asn Pro
225                 230                 235

<210> SEQ ID NO 6
<211> LENGTH: 24
<212> TYPE: PRT
<213> ORGANISM: Macaca fascicularis

<400> SEQUENCE: 6

Met Trp Val Leu Val Val Phe Leu Thr Leu Ser Val Thr Trp Ile Gly
1               5                   10                  15

Ala Ala Pro Leu Ile Leu Ser Arg
            20

<210> SEQ ID NO 7
<211> LENGTH: 783
<212> TYPE: DNA
<213> ORGANISM: Homo sapiens

<400> SEQUENCE: 7
atgtgggtcc cggttgtctt cctcaccctg tccgtgacgt ggattggtgc tgcacccctc      60
atcctgtctc ggattgtggg aggctgggag tgcgagaagc attcccaacc ctggcaggtg     120
cttgtggcct ctcgtggcag ggcagtctgc ggcggtgttc tggtgcaccc ccagtgggtc     180
ctcacagctg cccactgcat caggaacaaa agcgtgatct tgctgggtcg gcacagcctg     240
tttcatcctg aagacacagg ccaggtattt caggtcagcc acagcttccc acaccegetc     300 tacgatatga gcctcctgaa gaatcgattc ctcaggccag gtgatgactc cagccacgac     360
ctcatgctgc tccgcctgtc agagcctgcc gagctcacgg atgctgtgaa ggtcatggac     420
ctgcccaccc aggagccagc actggggacc acctgctacg cctcaggctg gggcagcatt     480
gaaccagagg agttcttgac cccaaagaaa cttcagtgtg tggacctcca tgttatttcc     540
aatgacgtgt gtgcgcaagt tcaccctcag aaggtgacca agttcatgct gtgtgctgga     600
cgctggacag ggggcaaaag cacctgctcg ggtgattctg ggggcccact tgtctgtaat     660
ggtgtgcttc aaggtatcac gtcatgggc agtgaaccat gtgccctgcc cgaaaggcct     720
tccctgtaca ccaaggtggt gcattaccgg aagtggatca aggacaccat cgtggccaac     780
ccc                                                                  783

<210> SEQ ID NO 8
<211> LENGTH: 261
<212> TYPE: PRT
<213> ORGANISM: Homo sapiens

<400> SEQUENCE: 8

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
```

```
                85                  90                  95
Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
            165                 170                 175

His Val Ile Ser Asn Asp Val Cys Ala Gln Val His Pro Gln Lys Val
        180                 185                 190

Thr Lys Phe Met Leu Cys Ala Gly Arg Trp Thr Gly Gly Lys Ser Thr
    195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
            245                 250                 255

Ile Val Ala Asn Pro
            260

<210> SEQ ID NO 9
<211> LENGTH: 783
<212> TYPE: DNA
<213> ORGANISM: Macaca mulatta

<400> SEQUENCE: 9
atgtgggttc tggttgtctt cctcaccctg tccgtgacgt ggattggcgc tgcacccctc      60
atcctgtctc ggattgtggg aggctggagt gcgagaagc attcccaacc ctggcaggtg     120
cttgtggcct ctcgtggcag ggcagtctgc ggggtgttc tggtgcaccc ccagtgggtc     180
ctcacagctg cccactgcat caggagcaac agcgtgatct tgctgggtcg cacaacccg      240 tattatcctg aagacacggg ccaggtgttt caggtcagcc acagcttccc acacccgctc    300
tacaacatga gcctcctgaa gaatcgatac ctcgggccag gtgatgactc cagccacgac    360
ctcatgctgc tccgcctgtc agagcctgcc gagatcacag atgctgtgca ggtcctggac    420
ctgcccacct gggagccaga gctggggacc acgtgctacg cctcaggctg ggcagcatc      480 gaaccggagg aacacttgac tccaaagaaa cttcagtgtg tggacctcca tattatttcc    540
aatgatgtgt gtgcgcaagt tcactctcag aaggtgacca agttcatgct gtgtgctgga    600
agctggatgg gcggcaaaag cacctgctcg ggtgattctg ggggcccact ggtctgtgac    660
ggtgtgcttc aaggtatcac gtcatgggc agtcaaccat gtgccctacc ccgaaggcct    720
tccctgtaca ccaaggtggt gcgttaccgg aagtggatcc aggacaccat catggcaaac    780
ccc                                                                   783

<210> SEQ ID NO 10
<211> LENGTH: 261
<212> TYPE: PRT
<213> ORGANISM: Macaca mulatta

<400> SEQUENCE: 10
```

```
Met Trp Val Leu Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Ser Asn Ser Val Ile Leu Leu Gly Arg His Asn Pro
65                  70                  75                  80

Tyr Tyr Pro Glu Asp Thr Gly Gln Val Phe Gln Val Ser His Ser Phe
                85                  90                  95

Pro His Pro Leu Tyr Asn Met Ser Leu Leu Lys Asn Arg Tyr Leu Gly
            100                 105                 110

Pro Gly Asp Asp Ser Ser His Asp Leu Met Leu Leu Arg Leu Ser Glu
        115                 120                 125

Pro Ala Glu Ile Thr Asp Ala Val Gln Val Leu Asp Leu Pro Thr Trp
130                 135                 140

Glu Pro Glu Leu Gly Thr Thr Cys Tyr Ala Ser Gly Trp Gly Ser Ile
145                 150                 155                 160

Glu Pro Glu Glu His Leu Thr Pro Lys Lys Leu Gln Cys Val Asp Leu
                165                 170                 175

His Ile Ile Ser Asn Asp Val Cys Ala Gln Val His Ser Gln Lys Val
            180                 185                 190

Thr Lys Phe Met Leu Cys Ala Gly Ser Trp Met Gly Gly Lys Ser Thr
        195                 200                 205

Cys Ser Gly Asp Ser Gly Gly Pro Leu Val Cys Asp Gly Val Leu Gln
210                 215                 220

Gly Ile Thr Ser Trp Gly Ser Gln Pro Cys Ala Leu Pro Arg Arg Pro
225                 230                 235                 240

Ser Leu Tyr Thr Lys Val Val Arg Tyr Arg Lys Trp Ile Gln Asp Thr
                245                 250                 255

Ile Met Ala Asn Pro
            260

<210> SEQ ID NO 11
<211> LENGTH: 24
<212> TYPE: DNA
<213> ORGANISM: Artificial Sequence
<220> FEATURE:
<223> OTHER INFORMATION: Forward PCR primer, with an introduced BamHI
      site, which anneals to the translation initiation sites of the
      Homo sapiens and Macaca mulatta PSA cDNAs.

<400> SEQUENCE: 11
ctggatccct gtgccaccat gtgg                                          24

<210> SEQ ID NO 12
<211> LENGTH: 24
<212> TYPE: DNA
<213> ORGANISM: Artificial Sequence
<220> FEATURE:
<223> OTHER INFORMATION: Reverse PCR primer, with an introduced BamHI
      site, which anneals to a conserved region in the 3' untranslated
      region of the Homo sapiens and Macaca mulatta PSA cDNAs.

<400> SEQUENCE: 12
ccggatcctg ctgatttctt ttcc                                          24
```

<210> SEQ ID NO 13
<211> LENGTH: 24
<212> TYPE: DNA
<213> ORGANISM: Artificial Sequence
<220> FEATURE:
<223> OTHER INFORMATION: Forward sequencing primer annealing to Macaca
      fascicularis PSA cDNA

<400> SEQUENCE: 13
ccagccacga cctcatgctg ctcc                                              24

<210> SEQ ID NO 14
<211> LENGTH: 23
<212> TYPE: DNA
<213> ORGANISM: Artificial Sequence
<220> FEATURE:
<223> OTHER INFORMATION: Reverse sequencing primer annealing to Macaca
      fascicularis PSA cDNA.

<400> SEQUENCE: 14
ccccagaatc acccgacagg tgc                                               23

<210> SEQ ID NO 15
<211> LENGTH: 24
<212> TYPE: DNA
<213> ORGANISM: Artificial Sequence
<220> FEATURE:
<223> OTHER INFORMATION: 5' RACE primer annealing to Macaca fascicularis
      PSA cDNA.

<400> SEQUENCE: 15
cgtcacggac agggtgagga agac                                              24

<210> SEQ ID NO 16
<211> LENGTH: 24
<212> TYPE: DNA
<213> ORGANISM: Artificial Sequence
<220> FEATURE:
<223> OTHER INFORMATION: 3' RACE primer annealing to Macaca fascicularis
      PSA cDNA.

<400> SEQUENCE: 16
ggaagtggag ccaggacacc atca                                              24

<210> SEQ ID NO 17
<211> LENGTH: 20
<212> TYPE: DNA
<213> ORGANISM: Artificial Sequence
<220> FEATURE:
<223> OTHER INFORMATION: Forward primer annealing to Macaca fascicularis
      PSA cDNA.

<400> SEQUENCE: 17
ccatgtacgt ggccatccag                                                   20

<210> SEQ ID NO 18
<211> LENGTH: 20
<212> TYPE: DNA
<213> ORGANISM: Artificial Sequence
<220> FEATURE:
<223> OTHER INFORMATION: Reverse primer annealing to Macaca fascicularis
      PSA cDNA.

<400> SEQUENCE: 18
tggtggtgaa gctgtagccg                                                   20

The invention claimed is:

1. An isolated polypeptide comprising a polypeptide having the sequence shown in SEQ ID NO: 3.

2. An isolated polypeptide comprising a polypeptide having the sequence shown in SEQ ID NO: 5.

3. Isolated full-length Cynomolgus prostate specific antigen (PSA) consisting of the amino acid sequence shown in SEQ ID NO: 3.

4. Isolated mature Cynomolgus PSA consisting of the amino acid sequence shown in SEQ ID NO: 5.

* * * * *